(12) United States Patent
Franklin

(10) Patent No.: US 10,232,142 B2
(45) Date of Patent: Mar. 19, 2019

(54) CONDUIT GUIDING TIP

(71) Applicant: Prytime Medical Devices, Inc., Boerne, TX (US)

(72) Inventor: Curtis J. Franklin, Lakewood, CO (US)

(73) Assignee: Prytime Medical Devices, Inc., Boerne, TX (US)

( * ) Notice: Subject to any disclaimer, the term of this patent is extended or adjusted under 35 U.S.C. 154(b) by 89 days.

(21) Appl. No.: 15/306,540

(22) PCT Filed: Jun. 10, 2015

(86) PCT No.: PCT/US2015/035061
§ 371 (c)(1),
(2) Date: Oct. 25, 2016

(87) PCT Pub. No.: WO2015/191685
PCT Pub. Date: Dec. 17, 2015

(65) Prior Publication Data
US 2017/0043123 A1   Feb. 16, 2017

Related U.S. Application Data

(60) Provisional application No. 62/010,297, filed on Jun. 10, 2014.

(51) Int. Cl.
*A61M 25/00* (2006.01)
*A61M 25/01* (2006.01)

(52) U.S. Cl.
CPC ..... *A61M 25/0068* (2013.01); *A61M 25/0074* (2013.01); *A61M 25/01* (2013.01); *A61M 2025/0081* (2013.01); *A61M 2025/0096* (2013.01)

(58) Field of Classification Search
CPC .......... A61M 25/0074; A61M 25/0041; A61M 25/0068; A61M 2025/0081; A61M 2025/0096
See application file for complete search history.

(56) References Cited

U.S. PATENT DOCUMENTS

| | | | |
|---|---|---|---|
| 2,156,289 | A | 5/1939 | Hoy |
| 4,464,172 | A | 8/1984 | Lichtenstein |
| 4,713,888 | A | 12/1987 | Broselow |
| 4,777,951 | A | 10/1988 | Cribier et al. |

(Continued)

FOREIGN PATENT DOCUMENTS

| EP | 1094861 B1 | 4/2005 |
|---|---|---|
| EP | 1658808 A1 | 5/2006 |

(Continued)

OTHER PUBLICATIONS

Extended European Search Report dated Jun. 26, 2017 in EP Application No. 14842370.

(Continued)

*Primary Examiner* — Nathan R Price
*Assistant Examiner* — Justin L Zamory
(74) *Attorney, Agent, or Firm* — Panitch Schwarze Belisario & Nadel LLP

(57) ABSTRACT

A catheter tip for guiding the catheter through a patient's blood vessels and keeping the catheter in large vessels and preventing entry into smaller branch vessels.

13 Claims, 17 Drawing Sheets

(56) References Cited

U.S. PATENT DOCUMENTS

| | | |
|---|---|---|
| 4,823,469 A | 4/1989 | Broselow |
| 4,865,549 A | 9/1989 | Sonsteby |
| 4,926,885 A | 5/1990 | Hinkle |
| 4,983,166 A | 1/1991 | Yamawaki |
| 5,135,494 A | 8/1992 | Engelson et al. |
| 5,169,386 A | 12/1992 | Becker et al. |
| 5,282,479 A | 2/1994 | Havran |
| 5,320,605 A | 6/1994 | Sahota |
| 5,383,856 A | 1/1995 | Bersin |
| 5,447,503 A | 9/1995 | Miller |
| 5,505,702 A | 4/1996 | Arney |
| 5,522,400 A | 6/1996 | Williams |
| 5,571,093 A | 11/1996 | Cruz et al. |
| 5,718,678 A | 2/1998 | Fleming, III |
| 5,738,652 A | 4/1998 | Boyd et al. |
| 5,911,702 A | 6/1999 | Romley et al. |
| 6,011,988 A | 1/2000 | Lynch et al. |
| 6,013,019 A | 1/2000 | Fischell et al. |
| 6,102,930 A | 8/2000 | Simmons, Jr. |
| 6,113,579 A | 9/2000 | Eidenschink et al. |
| 6,146,370 A | 11/2000 | Barbut |
| 6,161,547 A | 12/2000 | Barbut |
| 6,165,199 A | 12/2000 | Barbut |
| 6,190,356 B1 | 2/2001 | Bersin |
| 6,231,572 B1 | 5/2001 | Hart et al. |
| 6,248,121 B1 | 6/2001 | Nobles |
| 6,280,434 B1 * | 8/2001 | Kinoshita ......... A61M 25/0041 600/435 |
| 6,423,031 B1 | 7/2002 | Donlon |
| 6,453,572 B2 | 9/2002 | Cross et al. |
| 6,575,932 B1 | 6/2003 | O'Brien et al. |
| 6,579,221 B1 | 6/2003 | Peterson |
| 6,602,270 B2 | 8/2003 | Leschinsky et al. |
| 6,656,153 B1 | 12/2003 | Sakai et al. |
| 6,666,814 B2 | 12/2003 | Downey et al. |
| 6,669,679 B1 | 12/2003 | Savage et al. |
| 6,679,860 B2 | 1/2004 | Stiger |
| 6,695,811 B2 | 2/2004 | Samson et al. |
| 6,719,270 B2 | 4/2004 | Ozawa |
| 6,719,720 B1 | 4/2004 | Voelker et al. |
| 6,733,513 B2 | 5/2004 | Boyle et al. |
| 6,735,532 B2 | 5/2004 | Freed et al. |
| 6,736,790 B2 | 5/2004 | Barbut et al. |
| 6,746,462 B1 * | 6/2004 | Selmon ................ A61M 29/02 606/159 |
| 6,796,959 B2 | 9/2004 | Davis et al. |
| 6,936,056 B2 | 8/2005 | Nash et al. |
| 6,979,318 B1 | 12/2005 | McDonald et al. |
| 7,341,571 B1 | 3/2008 | Harris et al. |
| 7,434,326 B2 | 10/2008 | Gifford |
| 7,503,904 B2 | 3/2009 | Choi |
| 7,503,909 B2 | 3/2009 | Kusu et al. |
| 7,763,043 B2 | 7/2010 | Goodin et al. |
| 7,892,469 B2 | 2/2011 | Lim et al. |
| 7,909,810 B2 * | 3/2011 | Noone ................ A61M 25/10 604/104 |
| 7,951,186 B2 | 5/2011 | Eidenschink et al. |
| 7,951,819 B2 | 5/2011 | Niculescu-Duvaz et al. |
| 7,959,644 B2 | 6/2011 | Shriver |
| 8,088,103 B2 | 1/2012 | Teeslink et al. |
| 8,162,879 B2 | 4/2012 | Hattangadi et al. |
| 8,241,241 B2 | 8/2012 | Evans et al. |
| 8,262,611 B2 | 9/2012 | Teeslink et al. |
| 8,419,648 B2 | 4/2013 | Corl et al. |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,655,798 B2 | 2/2014 | Humphrey et al. |
| 8,672,868 B2 | 3/2014 | Simons |
| 8,747,358 B2 | 6/2014 | Trombley, III et al. |
| 8,814,900 B2 | 8/2014 | Fleming, III |
| 8,900,214 B2 | 12/2014 | Nance et al. |
| 8,948,848 B2 | 2/2015 | Merhi |
| 8,951,565 B2 | 2/2015 | McCarthy |
| 9,131,874 B2 | 9/2015 | Eliason et al. |
| D748,257 S | 1/2016 | Franklin |
| 9,414,843 B2 | 8/2016 | Pavcnik et al. |
| 9,474,882 B2 | 10/2016 | Franklin |
| 9,687,333 B2 | 6/2017 | Angel et al. |
| 2002/0193735 A1 | 12/2002 | Stiger |
| 2003/0032974 A1 | 2/2003 | Leschinsky et al. |
| 2003/0167038 A1 | 9/2003 | Yozu et al. |
| 2004/0073162 A1 | 4/2004 | Bleam et al. |
| 2004/0082935 A1 | 4/2004 | Lee et al. |
| 2004/0254528 A1 | 12/2004 | Adams et al. |
| 2005/0059931 A1 | 3/2005 | Garrison et al. |
| 2005/0148812 A1 | 7/2005 | Nigroni et al. |
| 2005/0261725 A1 | 11/2005 | Crawford et al. |
| 2007/0043307 A1 | 2/2007 | Raulerson et al. |
| 2007/0043409 A1 | 2/2007 | Brian et al. |
| 2007/0129466 A1 | 6/2007 | Kagawa et al. |
| 2007/0135830 A1 | 6/2007 | Schaeffer |
| 2007/0219466 A1 | 9/2007 | Tremulis et al. |
| 2007/0219488 A1 | 9/2007 | Francescatti |
| 2008/0027356 A1 | 1/2008 | Chen et al. |
| 2008/0082046 A1 | 4/2008 | Kato et al. |
| 2008/0082119 A1 | 4/2008 | Vitullo |
| 2008/0243067 A1 | 10/2008 | Rottenberg et al. |
| 2008/0262477 A1 | 10/2008 | Djaladat |
| 2009/0026595 A1 | 1/2009 | Kadoi |
| 2009/0062666 A1 | 3/2009 | Roteliuk |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0234915 A1 | 9/2010 | Herlich et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2011/0196412 A1 | 8/2011 | Levit et al. |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0215166 A1 | 8/2012 | Barki |
| 2012/0271231 A1 | 10/2012 | Agrawal |
| 2012/0302994 A1 | 11/2012 | Wilson et al. |
| 2013/0102926 A1 | 4/2013 | Eliason et al. |
| 2013/0102929 A1 | 4/2013 | Haight et al. |
| 2013/0190619 A1 | 7/2013 | Nudel |
| 2013/0281869 A1 | 10/2013 | Barbut et al. |
| 2013/0289607 A1 | 10/2013 | Pedersen et al. |
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0316012 A1 | 10/2014 | Freyman et al. |
| 2014/0378869 A1 | 12/2014 | Sela et al. |
| 2015/0012031 A1 | 1/2015 | Rago et al. |
| 2015/0039012 A1 | 2/2015 | Solar et al. |
| 2015/0367098 A1 | 12/2015 | Aggerholm et al. |
| 2016/0000446 A1 | 1/2016 | Eliason et al. |

FOREIGN PATENT DOCUMENTS

| | | |
|---|---|---|
| EP | 1911484 A2 | 4/2008 |
| EP | 2389974 A1 | 11/2011 |
| EP | 2716323 A1 | 4/2014 |
| GB | 2297259 A | 7/1996 |
| JP | H 03198868 A | 8/1991 |
| JP | H 09-164208 A | 6/1997 |
| JP | 2002505165 A | 2/2002 |
| JP | 2003535652 A | 12/2003 |
| JP | 200714820 A | 1/2007 |
| JP | 2008546471 A | 12/2008 |
| JP | 2011245300 A | 12/2011 |
| WO | 9220398 A1 | 11/1992 |

(56) References Cited

FOREIGN PATENT DOCUMENTS

| | | |
|---|---:|---|
| WO | 9713542 A1 | 4/1997 |
| WO | 9834670 A2 | 8/1998 |
| WO | 1999/24105 A2 | 5/1999 |
| WO | 9944666 A2 | 9/1999 |
| WO | 0197743 A2 | 12/2001 |
| WO | 2004049970 A2 | 6/2004 |
| WO | 2006135853 A2 | 12/2006 |
| WO | 2007001701 A1 | 1/2007 |
| WO | 2007022592 A1 | 3/2007 |
| WO | 2008013441 A1 | 1/2008 |
| WO | 2010070685 A1 | 6/2010 |
| WO | 2011133736 A2 | 10/2011 |
| WO | 2014/003809 A1 | 1/2014 |
| WO | 2014134215 A1 | 9/2014 |
| WO | 2014152191 A1 | 9/2014 |
| WO | 2015/006828 A1 | 1/2015 |
| WO | 2015035393 A1 | 3/2015 |
| WO | 2015191685 A1 | 12/2015 |
| WO | 2016149653 A2 | 9/2016 |

OTHER PUBLICATIONS

Int'l Preliminary Report dated Jul. 17, 2017 in Int'l Application No. PCT/US2016/023223.
Int'l Search Report and Written Opinioin dated Sep. 28, 2017 in Int'l Application No. PCT/US2017/035729.
Office Action dated Sep. 19, 2017 in JP Application No. 2015-559309.
Office Action dated Sep. 12, 2017 in JP Application No. 2016-546035.
Office Action dated Oct. 12, 2017 in CA Application No. 2,980,018.
Holcomb et al., "Causes of death in US Special Operations Forces in the global war on terrorism: 2001-2004," Annals of Surgery, vol. 245, No. 6, pp. 986-991 (2007).
Sohn et al., "Demographics, Treatment, and Early Outcomes in Penetrating Vascular Combat Trauma," Arch Surg, vol. 143, No. 8, pp. 783-787 (2008).
White et al., "The Epidemiology of Vascular Injury in the Wars in Iraq and Afghanistan," Annals of Surgery, vol. 253, No. 6, pp. 1184-1189.
Fenton et al., "Comparing risks of alternative medical diagnosis using Bayesian arguments," J. Biomed. Inf., vol. 43, pp. 485-495 (2010).
Patel et al., "Bayesian Designs for Device Clinical Trials," MDG Forum, Waltham, MA., Nov. 3, 2010, downloaded from web page: <http://www.cytel.com/pdfs/Patel_Bayes_Devices_Slides_11.18.10.pdf>.
Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.
Int'l Preliminary Report on Patentability dated Sep. 11, 2015 in Int'l Application No. PCT/US2014/018779.
Int'l Search Report and Written Opinion dated Jun. 8, 2014 in Int'l Application No. PCT/US2014/018779.
Int'l Search Report and Written Opinion dated Oct. 14, 2011 in Int'l Application No. PCT/US2011/033368.
Sandgren et al., "The Diameter of the Common Femoral Artery in Healthy Human: Influence of Sex, Age, and Body Size," Journal of Vascular Surgery, vol. 29, No. 3, pp. 503-510 (1999).
Sam II et al., "Blunt Traumatic Aortic Transection: Endoluminal Repair with Commercially Available Aortic Cuffs," Journal of Vascular Surgery, vol. 38, No. 5, pp. 1132-1135 (2003).
Peterson et al., "Percutaneous endovascular repair of blunt thoracic aortic transection," Journal of Trauma, vol. 59, No. 5, pp. 1062-1065 (2005).
Office Action dated Oct. 28, 2014 in U.S. Appl. No. 13/642,465.
Office Action dated Apr. 6, 2015 in U.S. Appl. No. 13/642,465.
Stannard et al., "Resuscitative Endovascular Balloon Occlusion of the Aorta (REBOA) as an Adjunct for Hemorrhagic Shock," J. Trauma, vol. 71, pp. 1869-1872 (2011).
Ledgerwood et al., "The Role of Thoracic Aortic Occlusion for Massive Hemoperitoneum," J Trauma, vol. 16, No. 8, pp. 610-615 (1976).
Detrano et al. "Bayesian Probability Analysis: a Prospective Demonstration of its Clinical Utility in Diagnosing Coronary Disease," Circulation, vol. 69, No. 3, pp. 541-547 (1984).
Int'l Search Report and Written Opinion dated Jan. 28, 2015 in Int'l Application No. PCT/US2014/054802.
Int'l Preliminary Report on Patentability dated Mar. 24, 2016 in Int'l Application No. PCT/US2014/054802.
Int'l Preliminary Report on Patentability dated Nov. 1, 2012 in Int'l Application No. PCT/US2011/033368.
Langewouters et al., "The static elastic properties of 45 human thoracic and 20 abdominal aortas in vitra and the parameters of a new model," Journal of Biometrics, vol. 17, No. 6, pp. 425-435 (1984).
Hughes, "Use of an Intra-Aortic Balloon Catheter Tamponade for Controlling Intra-Abdominal Hemorrhage in Man," Surgery, vol. 36, pp. 65-68 (1954).
Office Action dated Aug. 23, 2016 in AU Application No. 2015274743.
Extended European Search Report dated Oct. 5, 2016 in Europe Application No. EP 14 75 6640.
Supplemental Search Report dated Dec. 19, 2016 in EP Application No. 15806534.
Int'l Preliminary Report dated Dec. 22, 2016 in Int'l Application No. PCT/US2015/035061.
Int'l Search Report and Written Opinion dated Sep. 4, 2015 in Int'l Application No. PCT/US2014/035061.
Extended Search Report dated Mar. 24, 2017 in EP Application No. 14842370.
Int'l Search Report and Written Opinion dated Apr. 21, 2017 in Int'l Application No. PCT/US2016/023223.
Extended Search Report dated Mar. 21, 2017 in EP Application No. 15806534.
Office Action dated Apr. 11, 2017 in JP Application No. 2016-546035.
Office Action dated Mar. 20, 2017 in CA Application No. 2,797,237.
Chen et al., "The Renal Length Nomogram: A Multivariable Approach," The Journal of Urology, vol. 168, pp. 2149-2152 (Nov. 2002).

\* cited by examiner

CONDUIT GUIDING TIP

CROSS-REFERENCE TO RELATED APPLICATIONS

The present application is a national stage application under 35 U.S.C. § 371 of International Patent Application No. PCT/US2015/035061, filed Jun. 10, 2015 and titled, "Conduit Guiding Tip," which was published under International Publication No. WO 2015/191685 A1 and claims the benefit of U.S. Provisional Patent Application No. 62/010,297, filed on Jun. 10, 2014 titled, "Conduit Guiding Tip," the disclosures of which are incorporated herein by reference.

STATEMENT REGARDING FEDERALLY SPONSORED RESEARCH OR DEVELOPMENT

This invention was made with government support under Contract No. W81XWH-12-1-0558 awarded by U.S. Army Medical Research Materiel Command. The government has certain rights in the invention.

FIELD OF THE INVENTION

The invention generally relates to intravascular catheters, and more particularly to catheter tips for guiding the catheter through a patient's blood vessels during deployment.

BACKGROUND

Intravascular devices are devices that are generally placed within the lumen of a blood vessel during a therapeutic procedure. The therapeutic procedure may be any one of a wide variety of procedures, such as for example, stent delivery, angioplasty, atherectomy, embolic filtering, aortic occlusion, or any other therapeutic procedure performed in a blood vessel. The intravascular device used in such procedures typically include a catheter or guidewire for obtaining access to a desired location in a patient's blood vessel.

In general, the therapeutic procedures involve inserting a catheter or guidewire into a blood vessel such as the femoral artery. The catheter is then pushed into the blood vessel and into branches of blood vessels until the distal end of the catheter has reached a desired location within the patient's blood vessels. Once properly positioned, the therapeutic procedure is performed.

The path to the desired location in the patient's blood vessels is typically not an easy one. The blood vessels contain many branches into other blood vessels of varying sizes creating a tortuous path to almost any position in the body. Some applications use imaging to assist in properly placing the catheter. Radio opaque markers on strategic points on the catheter may be used to locate the parts of the catheter on an x-ray or other suitable form of imaging as the catheter is being placed. The use of imaging however requires special equipment often only available in specially equipped rooms in a hospital or other facility. There are intravascular procedures that may need to be performed on an emergency basis outside of a hospital setting. For example, a patient may require an aortic occlusion device to slow blood loss while at an accident site.

Even when a patient is in a hospital setting and requires a therapeutic procedure involving placing a catheter in the patient's blood vessels, it would be desirable to place the catheter without the need to use special imaging equipment. It would be desirable in some therapeutic procedures to have the option to administer a catheter from the patient's bedside without the need to transfer the patient to another room.

Another difficulty with placing a catheter is due to the construction of a typical catheter. Catheters typically extend distally to a tip. In some catheters, a guiding balloon near the tip is used to center the tip as the catheter winds its way through the tortuous path of the patient's blood vessels. Otherwise, the tip is pushed through the blood vessels without any real advantage for navigating the different branches that the catheter could follow.

There is a need in the art for a way to insert a catheter in a patient's blood vessels and to place the catheter at a desired location in the blood vessels without the need for special imaging equipment or for special facilities.

SUMMARY OF THE INVENTION

In view of the above, a device is provided for guiding a catheter through a patient's blood vessels. The device comprises a catheter guiding tip extending distally at a distal end of the catheter with an outer dimesion (sometimes referred to herein as "thickness") substantially the same as an outer dimension of the catheter. The catheter guiding tip has at least one guiding member that expands distally to a tip portion having a shape in an uncompressed state that is larger than the catheter outer dimension along at least one axis perpendicular to a longitudinal axis of the catheter. The catheter guiding tip is deformable for insertion in a sheath larger than the tip portion when the tip portion is compressed but smaller than the tip portion when the tip porion is not compressed and is resilient for resuming the shape in the uncompressed shape when not subject to compression forces.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention will become more apparent from the following detailed description of exemplary embodiments, read in conjunction with the accompanying drawings. The detailed description and drawings are merely illustrative of the invention rather than limiting, the scope of the invention being defined by the appended claims and equivalents thereof.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

Furthermore, the invention is described in the context of a catheter system. It will be understood that the catheter guiding tips may be used with catheters for a variety of different therapeutic or diagnostic indications involving vascular interventions, including, for example and without limitation, vascular occlusion, angioplasty, stent delivery, artherectomy, drug delivery, imaging or the like. Applications of catheter systems in which embodiments of the invention find advantageous use may utilize any suitable access site, such as, for example, the femoral artery, the brachial artery, the subclavian artery, or any other suitable blood vessel. In addition, applications in which embodiments of the invention find advantageous use may also involve venous as well as arterial blood vessels.

In the following description, when reference is made to the terms "proximal" or "proximally" it is intended to mean a portion or component of the catheter system that is oriented away from the body into which the system is or is intended to be placed. Conversely, when reference is made to the terms "distal" or "distally" it is intended to mean a portion or component of the catheter system that is oriented toward the body into which the system is or is intended to be placed. Thus, for example, the catheter guiding tip described hereinafter is located at a distal end of the catheter system, while the proximal hub is located at a proximal end of the catheter system.

Figure 1:
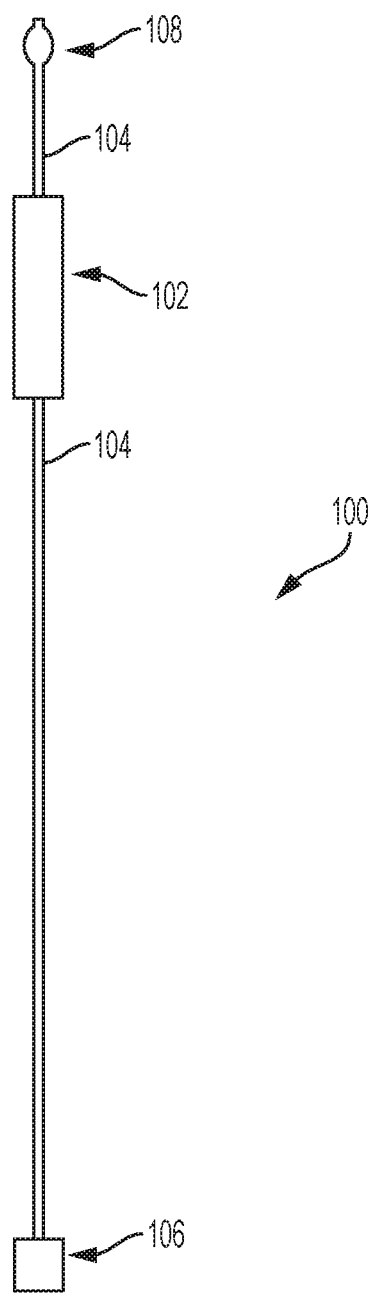
FIG. 1 is a schematic drawing of an example of a catheter system.

FIG. 1 is a schematic diagram of a catheter system 100 for performing an intravascular therapeutic procedure. The catheter system 100 comprises an intravascular device 102, a catheter member 104, a proximal hub 106, and a catheter guiding tip 108. The intravascular device 102 may be any mechanism, component, system or sub-system for performing a desired intravascular therapeutic procedure. Examples of the intravascular device 102 include, without limitation, a vascular occlusion device (e.g. occlusion balloon), an angioplasty device, a stent delivery system, an atherectomy system, a drug delivery system, an imaging system, an embolic filtering system, or the like.

The catheter member 104 may be any suitable wire, tube-like, or rod-like structure that may be fitted with the intravascular device 102 to extend into the patient's blood system, i.e., the patient's blood vessels, to position the intravascular device 102 at a desired location. The catheter member 104 may be made of a bio-compatible metal, such as a suitable metal alloy (e.g. nitinol) or stainless steel, or a bio-compatible polymer. The material of the catheter will typically be dictated by the therapeutic procedure, and on how long the catheter is to remain in the patient's blood vessels. The catheter member 104 may include one or more lumens that may be used, for example, to transport balloon filling fluids, to deliver drugs or other therapeutic materials such as thrombolyic agents, or to communicate with sensors.

The proximal hub 106 may be any suitable device for communicating between the proximal end of the catheter system 100 and the portions of the catheter in the blood vessels. The proximal hub 106 may include for example, ports or fittings (e.g. luer locks) for fluidly communicating with lumens in the catheter. In some examples, the proximal hub 106 may also provide a proximal endpoint or mechanisms (such as markings) for determining the positional extent of the catheter system 100 in the patient's blood vessels.

The catheter guiding tip 108 distally extends from a distal end of the catheter member 104 to a distal tip. The catheter guiding tip 108 extends from the catheter member 104 and expands distally to a tip portion. The tip portion has a shape in an uncompressed state that is larger than the catheter outer dimension along at least one axis perpendicular to a longitudinal axis of the catheter member 104. The catheter guiding tip 108 is deformable for insertion in a sheath during deployment and is resilient for resuming the shape in the uncompressed shape when not subject to compression forces.

The catheter guiding tip 108 may be an extension of the catheter member 104 and made of the same material as the catheter member 104. Alternatively, the catheter guiding tip 104 may be a component that is fixedly attached to a distal end of the catheter member 104. The catheter guiding tip 108 may have a shape and size in an uncompressed state that assists in guiding the catheter through the tortuous paths of the blood vessel. The catheter guiding tip 108 also has a shape that renders the tip atraumatic so as to prevent damage to the blood vessels during deployment.

Figure 2A:
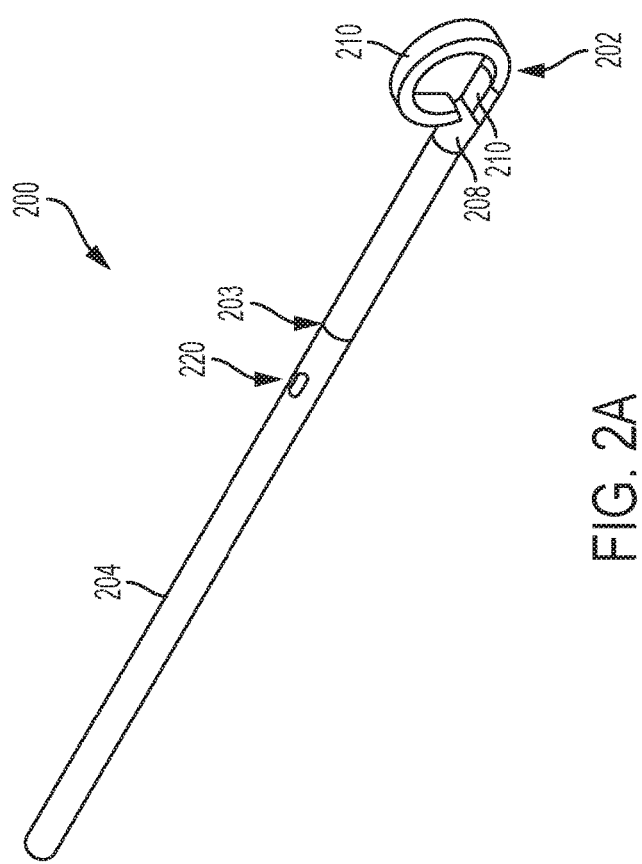
FIGS. 2A-2G are different views of an example catheter guiding tip.
Figure 2B:
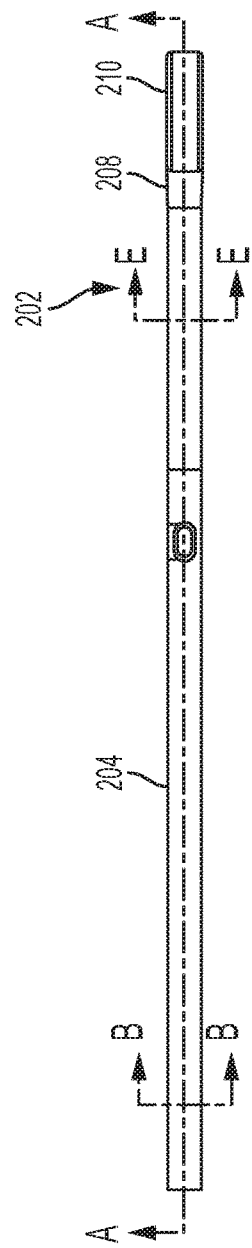
Figure 2C:
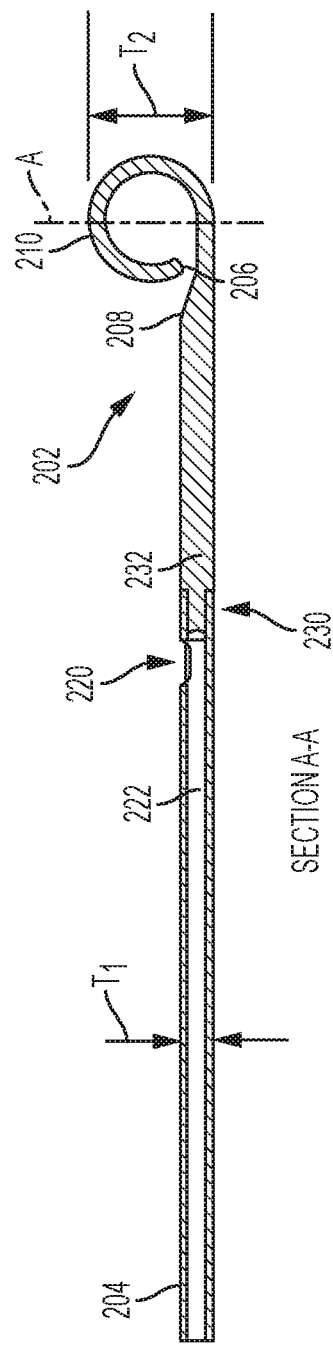
Figure 2D:
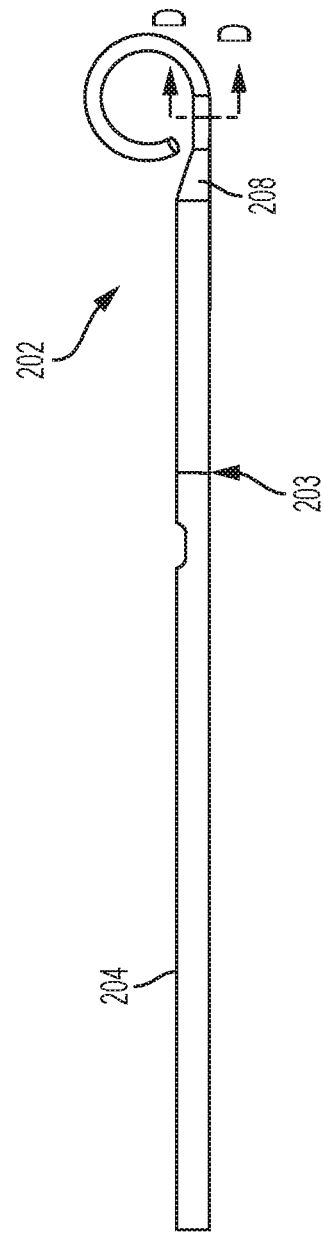

FIGS. 2A-2G are different views of an example catheter guiding tip 200. The catheter guiding tip 200 comprises a tip portion 202 extending from a catheter member 204 at a connection point 203. As shown in FIG. 2C, which is a cross-sectional view at section A-A of FIG. 2B, the catheter member 204 has an outer dimension (thickness) $T_1$ and the tip portion 202 extends from the connection point 203 at substantially the same outer dimension. The tip portion 202 extends to a transition section 208 where the tip portion 202 begins to transition from a solid or tubular generally or substantially cylindrical cross-section to a flattened solid or tubular cross-section at a coiled section 210. At the coiled section 210, the tip portion 202 has a shape in an uncompressed state with an outer dimension that is larger at $T_2$ than the outer dimension $T_1$ of the catheter along axis A, which is perpendicular to a longitudinal axis of the catheter member 204. The size $T_2$ of the tip portion 202 in an uncompressed state is sufficiently large to prevent the tip portion 202 from entering smaller blood vessels as the catheter member 204 is inserted in the blood vessels.

Figure 2E:
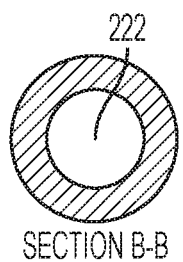
Figure 2F:
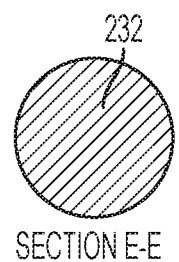

The catheter member 204 may include a catheter lumen 222 as shown in FIG. 2C and in FIG. 2E, which is a cross-sectional view of the catheter member 204 at section B-B of FIG. 2B. The catheter member 204 may also include a catheter opening 220 in fluid communication with the lumen 222. The catheter opening 220 may be used to deliver drugs or thrombolytic agents through the catheter member 204 into the blood vessel. The catheter opening 220 may also be used for sensors or for any other function depending on the particular application of the catheter system. The tip portion 202 may be solid as shown at 232 in FIG. 2C and in FIG. 2F, which is a cross-sectional view of the tip portion 202 at section E-E in FIG. 2B. Alternatively, the tip portion 202 may be a hollow tube or tubular member. The tip portion 202 may include a narrowed portion at 230 that fits into the lumen 222 of the catheter member 204 at connection point 203. The tip portion 202 may be attached to the catheter member 204 by overmolding the tip portion 202 to the catheter member 204, or so that the tip portion 202 and the catheter member are thermally welded at 230 by any method. in some example implementations, the attachment may be accomplished by radio frequency energy applied to the tip portion 202 and the catheter member 204 at the location where they are joined, such as at the region of the connection point 203. Any other suitable method or equipment may be used for the connection between the tip portion 202 and the catheter 204. Thus, for further examples, other techniques include the use of laser welding, ultrasonic welding, a hot air nozzle or a hot jaw bonder, or a split die bonder could be used to make the thermal connection. In still other example implementations, an adhesive may be used to secure the bond between the tip portion 202 and catheter member 204.

The shape of the tip portion 202 of the catheter guiding tip 200 in FIGS. 2A-2G has a shape in an uncompressed state that is formed as a solid or tubular member extending distally, then flattens at transition section 208 to the flattened solid or tubular cross-section extending radially to form the coiled section 210 at an axis A that is perpendicular to the longitudinal axis of the catheter member 204. The coiled section 210 may hook circularly around such that a most distal point 206 of the tip portion 202 is positioned at or beyond a transition section 208 where the catheter 204 begins to flatten to the coiled section 210. This ensures that the most distal point 206 is somewhat tucked into the curl of the tip portion 202. If the most distal point 206 of the tip portion 202 does not extend to at least the transition point 208, it is possible that the most distal point 206 of the tip portion 202 may catch on something on the blood vessel wall (such as a stent, plaque, a dissection, or other devices) during extraction of the catheter. For example, in an example implementation in which the catheter system is deployed to apply a stent in a blood vessel, the tip portion 202 would be distal the location of the stent. During extraction after the stent has been placed in the blood vessel, the tip portion 202 would move past the stent. If the tip portion 202 were a simple hook in which the most distal point 206 only reaches part of the way around towards the transition point 208, there is a danger that the most distal point 206 of the tip portion 202 may catch on the stent as it moves past the stent during extraction of the catheter.

Figure 2G:
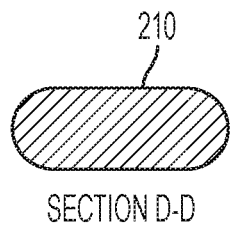

In the example shown in FIGS. 2A-2G, and particularly in FIG. 2G, the coiled section 210 has a solid or tubular flattened cross-section. FIG. 2G is an exemplary cross-section view of the coiled section 210 at section D-D when the tip portion 202 is a solid material. During deployment, the coiled section 210 is straightened for insertion into a sheath that is inserted into a blood vessel. Once the coiled section 210 is moved past the sheath and into the blood vessel, the coiled section 210 resumes its coiled shape. The flattened solid or tubular cross-section of the coiled section 210 permits the coiled section to resume its coiled shape so that the distal most point 206 is substantially aligned with the coiled section 210 and not skewed towards one side or the other.

In an example implementation of the tip portion 202 described with reference to FIGS. 2A-2G, the tip portion 202 may be made of an injection molded plastic material that is relatively supple so that the tip portion 202 may be compressed or deformed by extending the tip portion 202 along a longitudinal axis of the catheter member 204, yet resilient so as to resume its shape when no longer subject to compression or deformation forces. For example, the tip portion 202 may be made of a resilient thermoplastic elastomer plastic material, such as thermoplastic polyurethane or a polymeric or copolymeric polyether block amide, such as a PEBAX® engineering thermoplastic elastomer. The tip portion 202 may also be made of a flexible metal material that may be compressed or re-shaped by extending the tip portion 202 to straighten the tip portion 202 along a longitudinal axis of the catheter member 204, such as a shaped nitinol metal. When the tip portion 202 is uncompressed, the tip portion 202 reverts back to its uncompressed shape. If desired, the metal tip portion 202 may be coated or covered with a jacket plastic material, such that the tip portion 202 may remain or be enhanced to be compressible and resilient when the compression force is released.

The tip portion 108 (and corresponding parts of the various embodiments) of the catheter systems 100 (and corresponding parts of the various embodiments), have a very soft, atraumatic tip to prevent the tip from perforating or tearing the blood vessel into which inserted as it is advanced through the blood vessel. Catheter shafts, in general, need to be stiffer to offer pushability and prevent buckling. Therefore the tip portion of the catheter system transitions from a relatively stiff shaft section to a very soft tip. The transition can occur in one step or over a series of steps. By way of example and not limitation, one embodiment of the catheter system 200 of the present invention (and corresponding parts of the various embodiments) has a catheter member 204, made of a PEBAX® polymer with a 72 durometer (D) hardness, with a coaxial nitinol hypotube running down the central lumen 222. This catheter member is rather stiff to have good pushability and also withstand aortic occlusion. The nitinol hypotube terminates just distal of any expansible members, such as a balloon that may be carried by the catheter system, but the catheter member still is a PEBAX® polymer with a 72 D hardness. The catheter tip portion 202 is softer, and has a significantly lower hardness, such as 40 D, but may also be made of a PEBAX® polymer to make the tip atraumatic. Some catheter systems transition from high durometers of the catheter member 204 to tip portions 204 having lower durometers over multiple steps (e.g. 72 D, 60 D, 55 D, 40 D, 35 D, etc), usually depending on the rest of the catheter design.

Additionally, it is often helpful to transition from a catheter member 204 made of a PEBAX® polymer as a tubular member with a hardness of 72 D to a solid tip portion 202 made of a PEBAX® polymer with a hardness of 40 D. If the tip portion, even if made of a PEBAX® polymer with a hardness of 40 D were a tube, rather than a solid, it may not function as well, since it may collapse, kink, be too flimsy, etc. However, the hardness of the tip portion can be adjusted to be an atraumatic tip based on the construction of the tip portion, its shape, whether it is tubular or solid, or the like, in view of the description herein.

To prepare for insertion into the patient's vascular system, by means of an introducer sheath, the tip portion 202 may be straightened in a compressed state to ease insertion into the valve of the introducer sheath. Introducer sheaths are commonly used to provide access to blood vessels, such as the femoral artery, and often have a hemostasis valve to minimize blood loss. A peel-away sheath insertion tool can be used to straighten the tip portion 202 into a compressed state to ease insertion of the catheter tip past the introducer sheath valve. A peel-away sheath is often comprised of a plastic tube that can be peeled apart after assisting the insertion of the catheter into the introducer sheath to separate it from the catheter. Once the tip portion 202 exits the introducer sheath, it may automatically re-shape to its shape in an uncompressed or undeformed state as shown in FIG. 2A. The shape of the tip portion 202 may be used as a guide to ensure that the catheter is following the desired path through the blood vessels.

It is noted that the tip portion 202 of the catheter guiding tip 200 in the examples illustrated in FIGS. 2A-2G is attached to a distal end of the catheter member 204. In other example implementations, the catheter guiding tip 200 may be formed as an extension of the catheter member 204. The tip portion 202 in the examples illustrated in FIGS. 2A-2G also has a solid core. The tip portion 202 in other example implementations may include a lumen or a hollow core to provide further pliability if so desired. The tip portion 202 of the catheter guiding tip 200 in the examples in FIGS. 2A-2G is also shaped as a curled, or coiled member. However, the tip portion in other example implementations may have any suitable shape that expands to a size greater than the outer dimension of the catheter member and sufficient to enter larger blood vessels such as the aorta, and not smaller blood vessels.

Figure 3A:
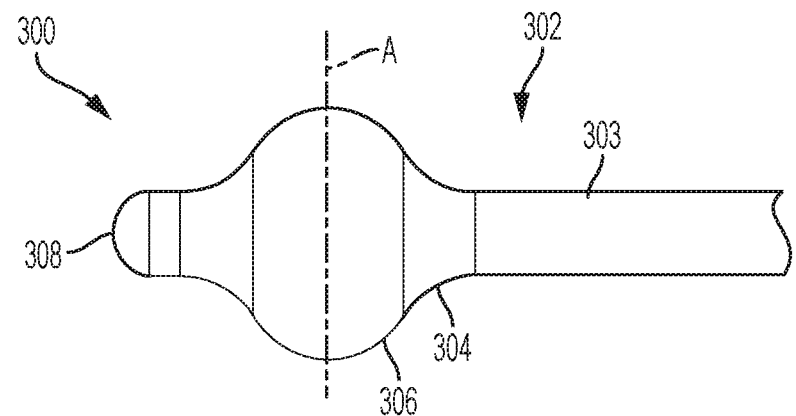
FIGS. 3A-3C are different views of another example catheter guiding tip.
Figure 3B:
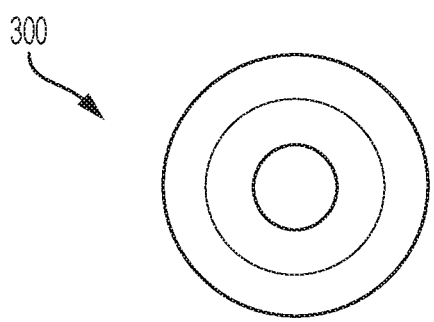
Figure 3C:
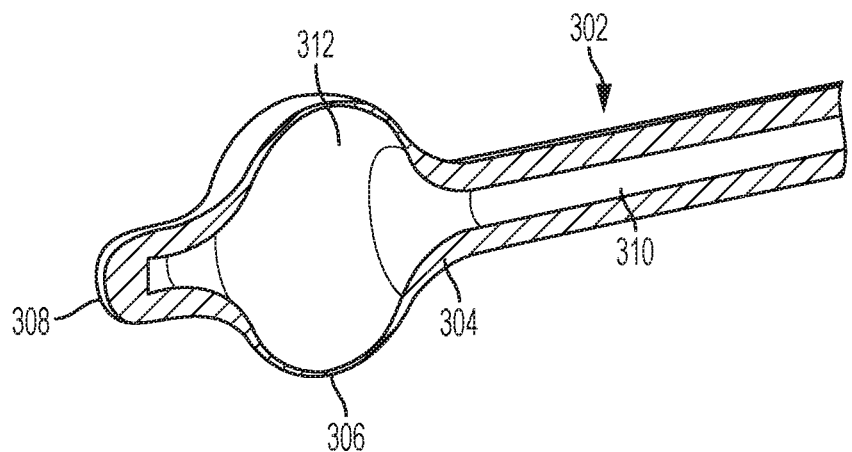

FIGS. 3A-3C are different views of another example catheter guiding tip 300. The catheter guiding tip 300 includes a tip portion 302 extending from a catheter member (not shown). The top portion 302 extends along a catheter connection portion 303 to a transition section 304 where the tip portion 302 expands in size to form a bulbous section 306. The bulbous section 306 of the tip portion 302 has a shape with an overall outer dimension in an undeformed state that is larger along axis A, which is perpendicular to a longitudinal axis of the catheter member, than the outer dimension of the catheter member. The tip portion 302 extends distally from the bulbous section 306 to a distal tubular extension 308. As shown in FIG. 3C, the catheter connection portion 303 of the tip portion 302 includes an inner space 310 extending longitudinally towards the bulbous section 306, which also includes a tip portion inner space 312. The inner space 310 and the tip portion inner space 312 allow the catheter connection portion 303 and tip portion 302 to be supple and resilient so the catheter guiding tip 300 is deformable and resumes its bulbous shape when not subject to compressing forces. The suppleness and resilience of the tip portion 302 may depend on the properties of the material of which the tip portion 302 is made and on the dimension between the outer surface of the tip portion 302 and the inner surface of the tip portion inner space 312.

Figure 4A:
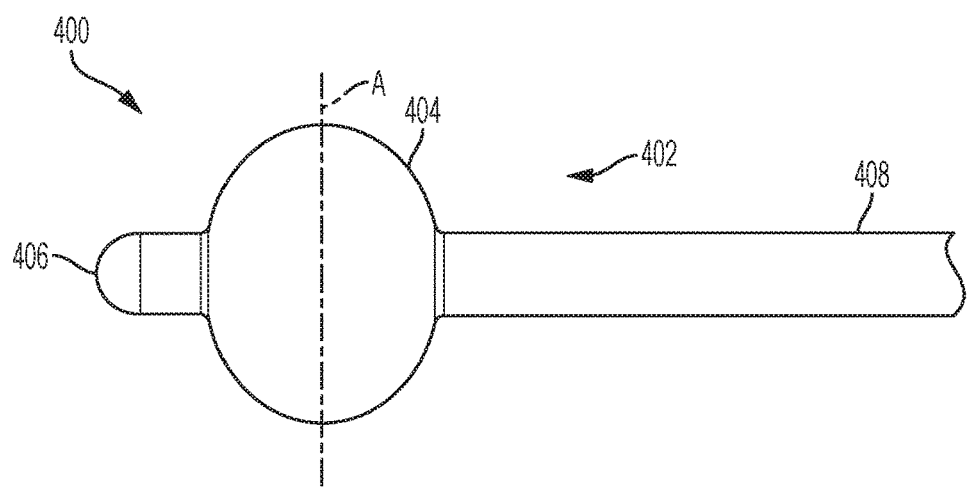
FIGS. 4A-4C are different views of another example catheter guiding tip.
Figure 4B:
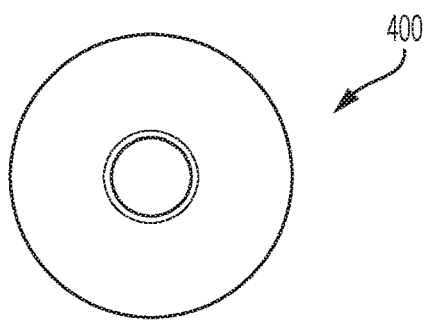
Figure 4C:
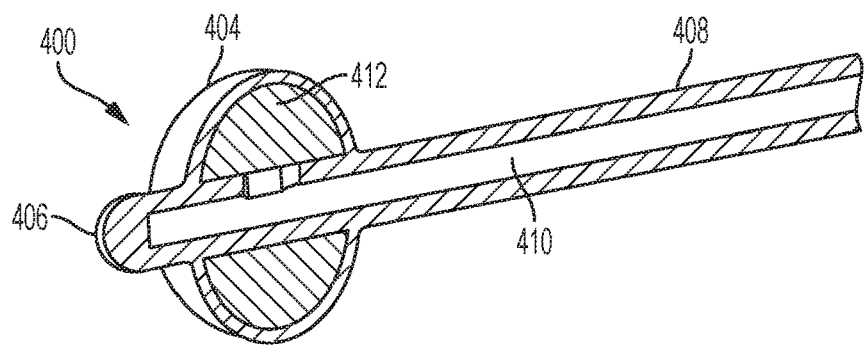

FIGS. 4A-4C are different views of another example catheter guiding tip 400. The catheter guiding tip 400 includes a tip portion 402 extending from a catheter member (not shown) along a catheter connection portion 408. The tip portion 402 has a bulbous shape 404 similar to that of the tip portion 302 in the catheter guiding tip 300 in FIGS. 3A-3C. The tip portion 402 extends distally from the bulbous shape 404 to a distal solid or tubular extension 406. The catheter connection portion 408 may extend to and through the bulbous shape 404 of the tip portion 402 with a catheter inner space 410 extending through the catheter connection portion 408. It is noted that the catheter connection portion 408 may be a solid or tubular section of the tip portion 402 that connects to a distal end of the catheter member as described above with reference to FIGS. 2A-2G. Alternatively, the catheter connection portion 408 and the tip portion 402 may be an extension of the catheter member.

The bulbous shape 404 of the tip portion 402 may include a space filler 412 in the inner space of the bulbous shape 404. The space filler 412 may be made of foam, porous plastic or any other suitable compressible material and may be formed unitarily with the bulbous shape 404 or separately inserted or attached within the bulbous shape. In an example embodiment, the inner space of the bulbous shape 404 may simply be air.

Figure 5A:
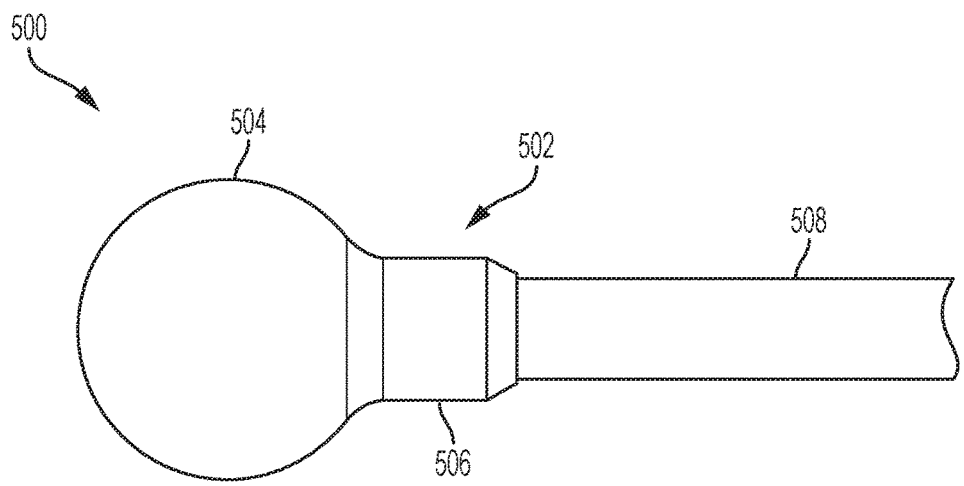
FIGS. 5A-5C are different views of another example catheter guiding tip.
Figure 5B:
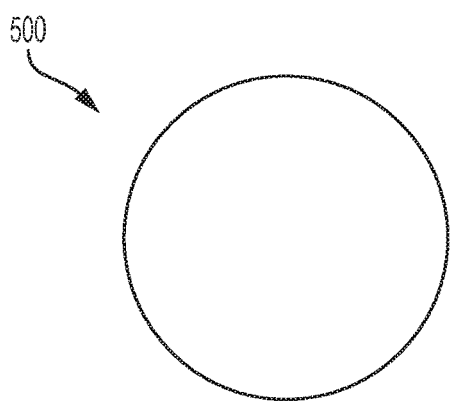
Figure 5C:
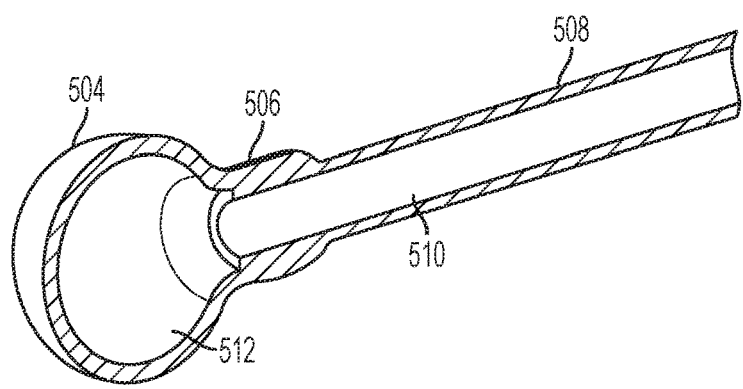

FIGS. 5A-5C are different views of another example catheter guiding tip 500. The catheter guiding tip 500 includes a tip portion 502 extending from catheter connection portion 508 of the tip portion 502. The catheter connection portion 508 may attach to a catheter member (not shown) as described above with reference to FIGS. 2A-2G. The tip portion 502 has a bulbous shape 504 similar to that of the tip portion 402 in the catheter guiding tip 400 in FIGS. 4A-4C except that the tip portion 502 does not have a tubular extension like tubular extensions 308 or 406 of FIGS. 3A-3C or FIGS. 4A-4C, respectively, that extends distally from the bulbous shape 504. The catheter connection portion 508 extends to a transition section 506 that connects the bulbous shape 504 of the tip portion 702 to the catheter connection portion 508. The catheter connection portion 508 has a catheter inner space 510 extending through the length of the catheter connection portion 508. The transition section 506 is a section with an outer dimension greater than the outer dimension of the catheter connection member 508, providing a stiffness in the transition between the straight catheter connection portion 508 and the bulbous shape 504. The bulbous shape 504 has a tip portion inner space 512 to allow bulbous shape 504 of the tip portion 502 to deform when subject to compression forces. The tip portion inner space 512 may be filled with foam or other compressible material.

Figure 6A:
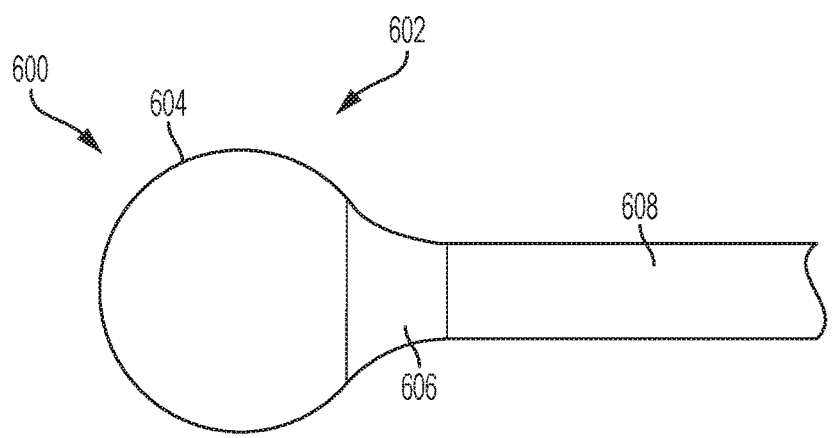
FIGS. 6A-6C are different views of another example catheter guiding tip.
Figure 6B:
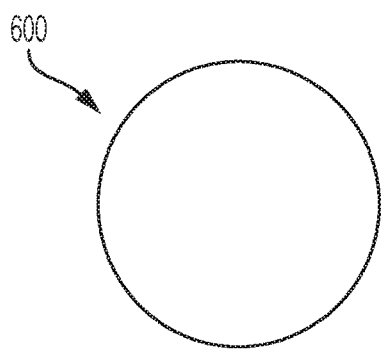
Figure 6C:
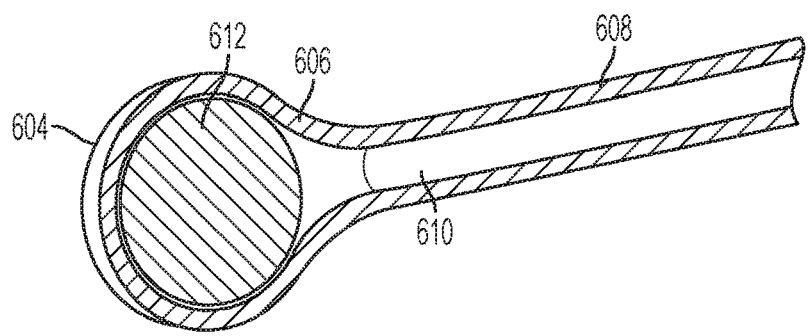

FIGS. 6A-6C are different views of another example catheter guiding tip 600. The catheter guiding tip 600 includes a tip portion 602 extending from a catheter connection portion 608 for connecting to a catheter member (not shown). The catheter connection portion 608 extends to a transition section 606, which expands to a bulbous shape 604 similar to that of the tip portion 502 in the catheter guiding tip 500 in FIGS. 5A-5C. The catheter connection portion 608 has a catheter inner space 610 extending through the length of the catheter connection portion 608. The transition section 606 expands into the bulbous shape 604 without any enlargement of the outer dimension of the transition section 606. The bulbous shape 604 has an inner space, which is filled in the example shown in FIG. 6C with a compressible material 612. In another example, the inner space of the bulbous shape 604 is filed with air.

Figure 7A:
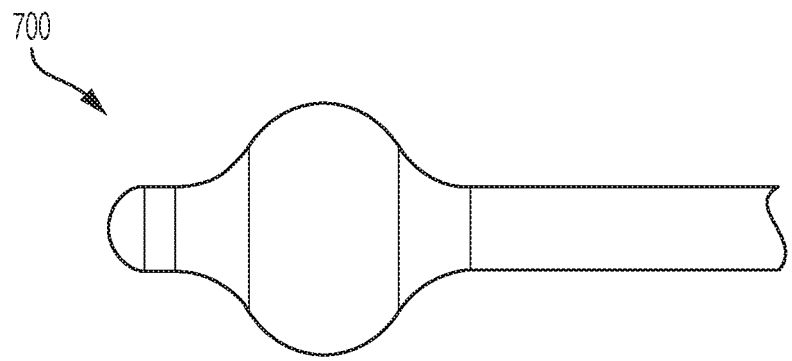
FIGS. 7A-7C are different views of another example catheter guiding tip.
Figure 7B:
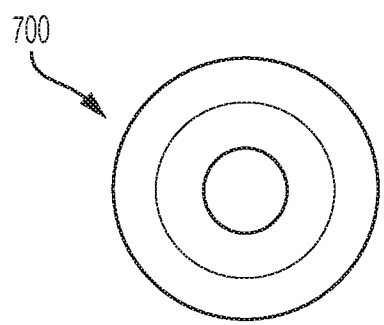
Figure 7C:
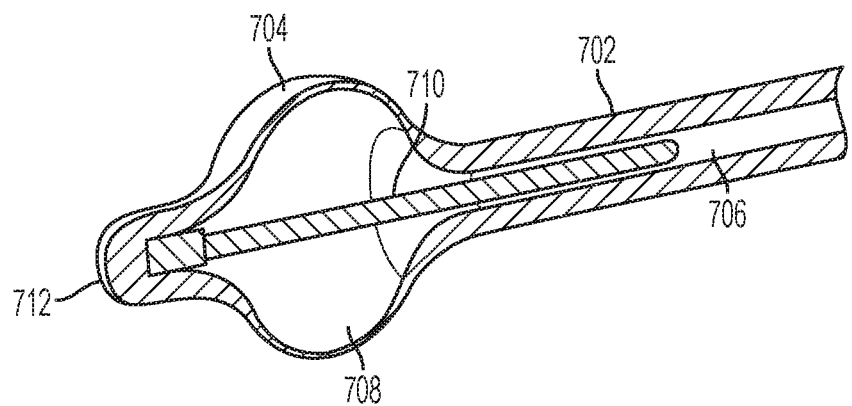

FIGS. 7A-7C are different views of another example catheter guiding tip 700. The catheter guiding tip 700 is similar to the catheter guiding tip 300 in FIGS. 3A-3C. The catheter guiding tip 700 in FIGS. 7A-7C includes a catheter connection portion 702, which extends distally to a bulbous shape 704. The catheter connection portion 702 includes an inner space 706 and the bulbous shape 704 includes a tip portion inner space 708 similar to the catheter guiding tip 300 in FIGS. 3A-3C. The catheter guiding tip 700 also extends distally from the bulbous shape 704 to a distal tubular extension 712. An alignment pin 710 is fitted in the inner space 706 of the catheter connection portion 702 and extends distally through the tip portion inner space 708 into the distal tubular extension 712. The alignment pin 710 may be made of any suitable material so that the alignment pin 710 is stiffer than the bulbous shape 704. The alignment pin 710 ensures that the distal tubular extension 712 extends distally during radial compression while keeping the distal tubular extension 712 on the same axis as the catheter connection portion 702 (as well as the catheter itself). The alignment pin 710 prevents the catheter guiding tip 700 from folding on itself.

Figure 8A:
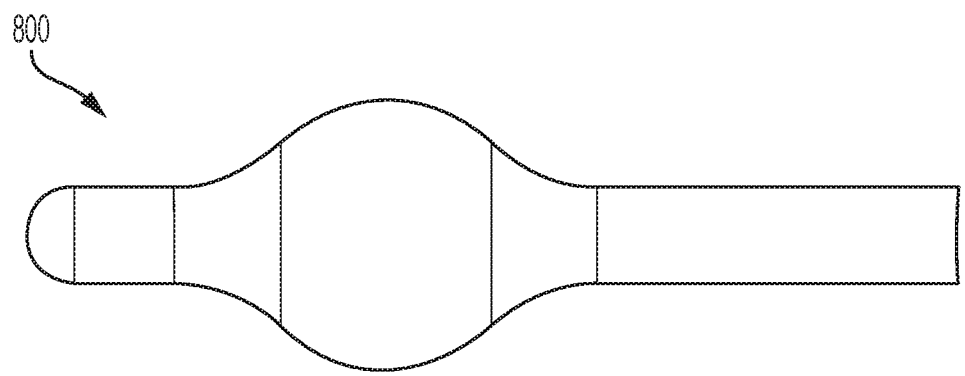
FIGS. 8A-8C are different views of another example catheter guiding tip.
Figure 8B:
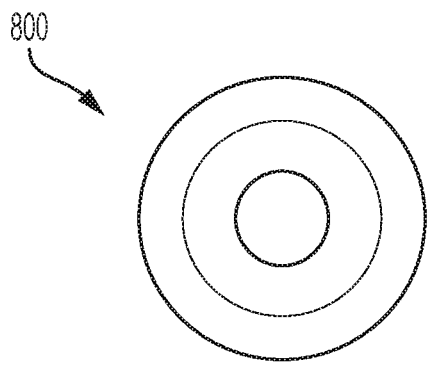
Figure 8C:
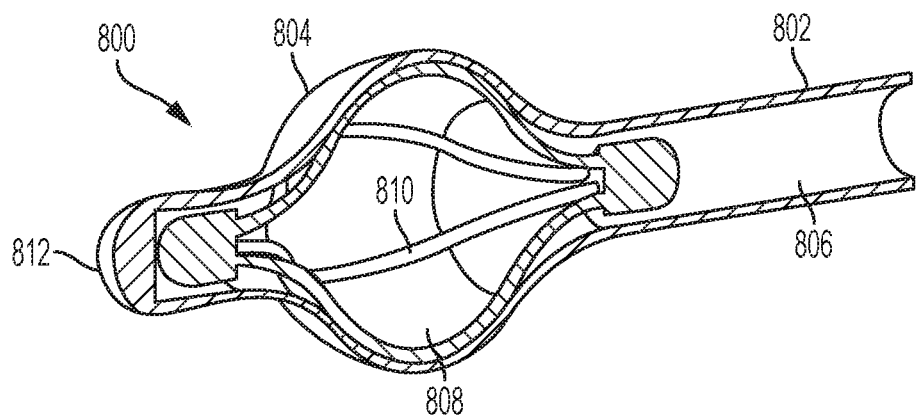

FIGS. 8A-8C are different views of another example catheter guiding tip 800. The catheter guiding tip 800 is also similar to the catheter guiding tip 300 in FIGS. 3A-3C. The catheter guiding tip 800 in FIGS. 8A-8C includes a catheter connection portion 802, which extends distally to a bulbous shape 804. The catheter connection portion 802 includes an inner space 806 and the bulbous shape 804 includes a tip portion inner space 808 similar to the catheter guiding tip 300 in FIGS. 3A-3C. The catheter guiding tip 800 also extends distally from the bulbous shape 804 to a distal solid or tubular extension 812. The bulbous shape 804 includes a bulbous shape frame 810 extending from the inner space 806 of the catheter connection portion 802 into the tip portion inner space 808 and is secured distally in the solid or distal tubular extension 812. The bulbous shape frame 810 may be made of any suitable material so that the bulbous shape frame 810 stiffens the bulbous shape 804, but yet remains compressible. The bulbous shape frame 810 ensures that the distal solid or tubular extension 812 extends distally during radial compression while keeping the distal solid or tubular extension 812 on the same axis as the catheter connection portion 802 (as well as the catheter itself). The bulbous shape frame 810 also prevents the catheter guiding tip 800 from folding on itself.

Figure 9A:
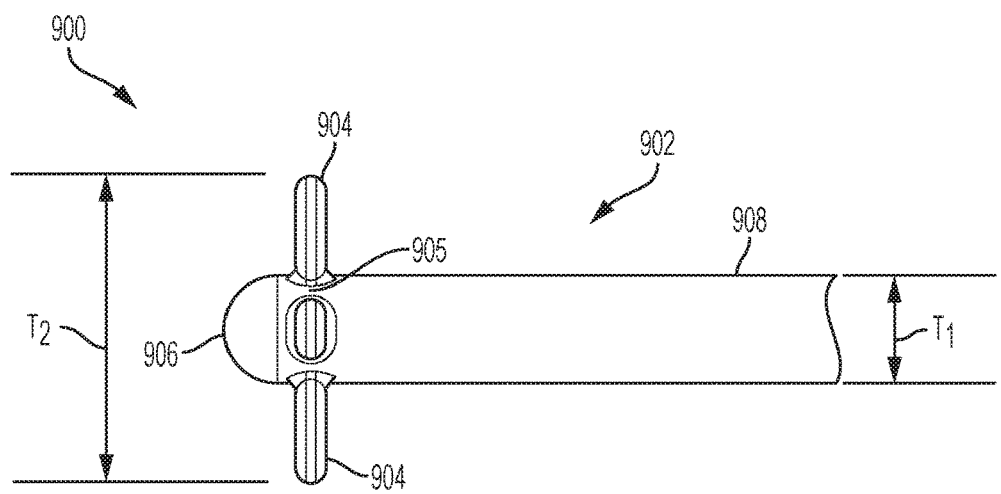
FIGS. 9A-9C are different views of another example catheter guiding tip.
Figure 9B:
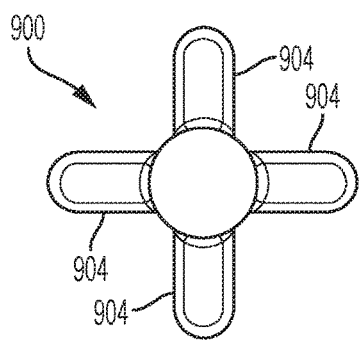
Figure 9C:
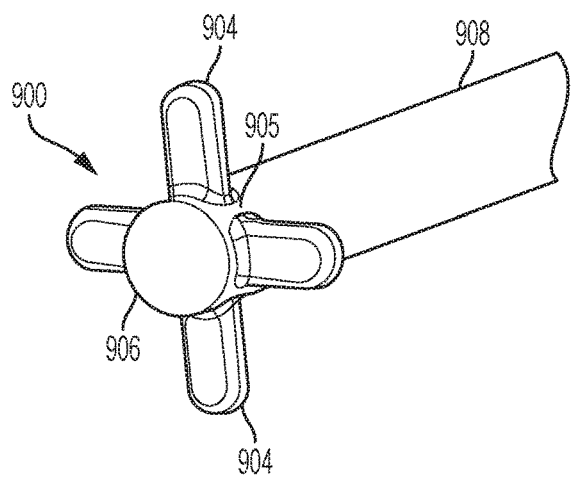

FIGS. 9A-9C are different views of another example catheter guiding tip 900. The catheter guiding tip 900 includes a tip portion 902 comprising a plurality of guiding members 904 extending radially from a solid or tubular portion 905 that extends from a catheter connection portion 908. The solid or tubular portion 905 extends beyond the at least one guiding member 904 to a distal solid or tubular tip 906. The plurality of guiding members 904 shown in FIGS. 9A-9C are substantially flattened members radiating from the solid or tubular portion 905 so that the tip portion 902 expands to a dimension $T_2$ that is larger than the outer dimension $T_1$ of the catheter connection portion 908 to prevent the tip portion 902 from entering smaller blood vessels as the catheter is inserted in the patient's blood vessels during deployment. The guiding members 904 are flattened perpendicular to a longitudinal axis of the catheter connection portion 908. The tip portion 902 in FIGS. 9A-9C may be made of an injection molded plastic that is compressible so that the tip portion 902 may be deformed under compression forces, yet resilient so that the tip portion 902 returns to its normal shape when compression forces are removed.

Figure 10A:
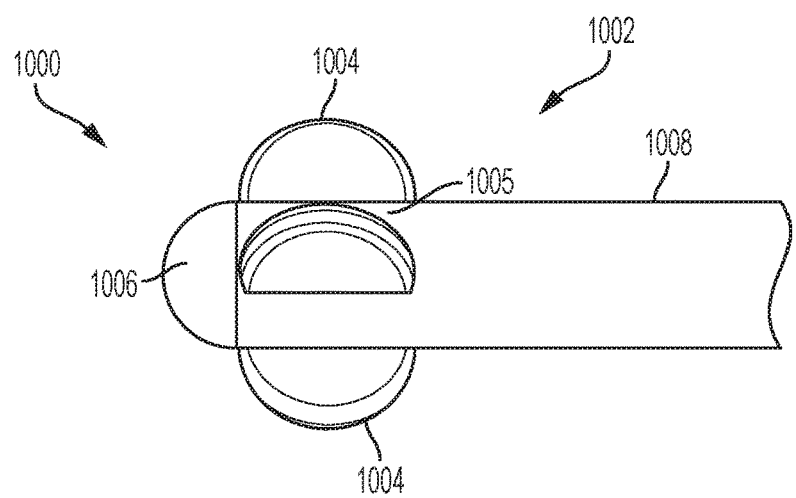
FIGS. 10A-10C are different views of another example catheter guiding tip.
Figure 10B:
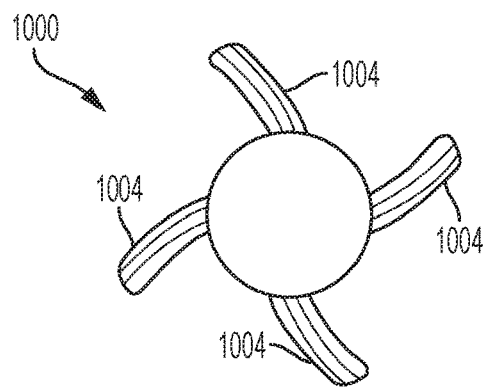
Figure 10C:
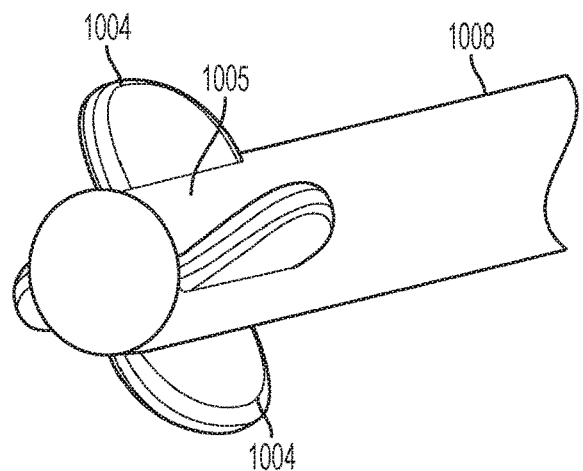

FIGS. 10A-10C are different views of another example catheter guiding tip 1000. The catheter guiding tip 1000 includes a tip portion 1002 comprising a plurality of guiding members 1004 extending radially from a solid or tubular portion 1005 that extends distally from a catheter connection portion 1008. The tubular portion 1005 extends beyond the at least one guiding member 1004 to a distal solid or tubular tip 1006. The plurality of guiding members 1004 shown in FIGS. 10A-10C are longitudinally flattened members radiating along a curve from the solid or tubular portion 1005. The guiding members 1004 in FIGS. 10A-10C extend radially as curved members as shown in FIG. 10B. However, in another embodiment, the guiding members 1004 may also extend as straight extending members. The tip portion 1002 in FIGS. 10A-10C may also be made of an injection molded plastic that is compressible.

Figure 11A:
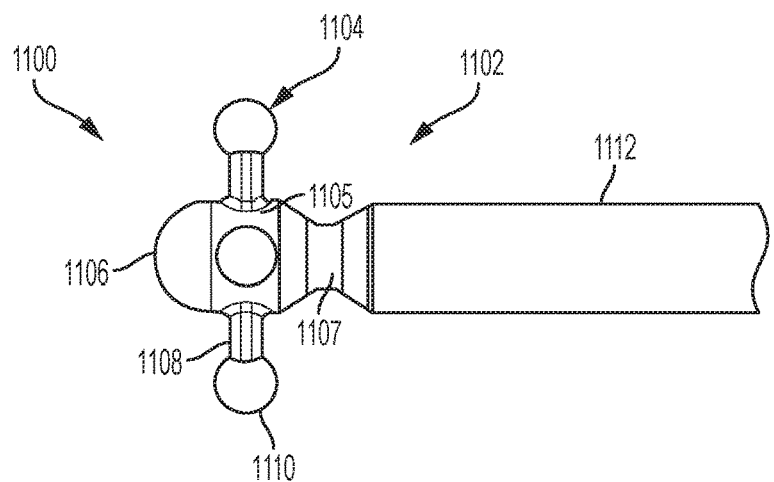
FIGS. 11A-11C are different views of another example catheter guiding tip.
Figure 11B:
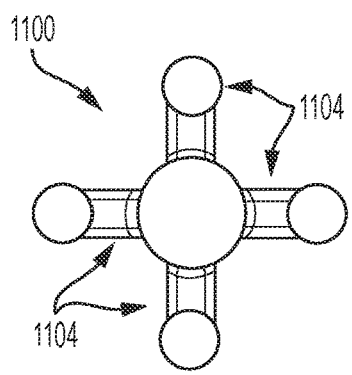
Figure 11C:
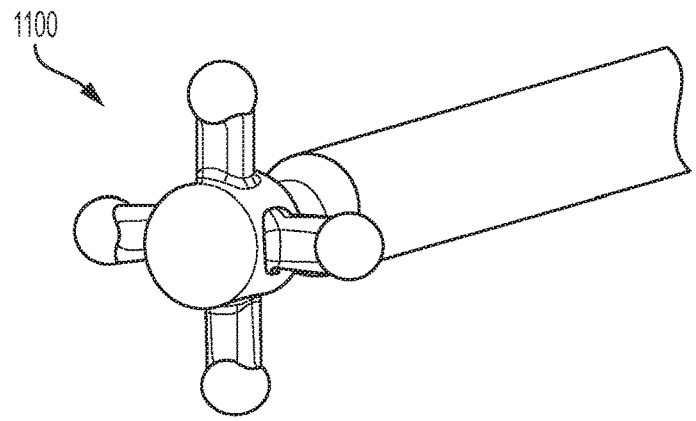

FIGS. 11A-11C are different views of another example catheter guiding tip 1100. The catheter guiding tip 1100 includes a tip portion 1102 comprising a plurality of guiding members 1104 extending radially from a solid or tubular portion 1105 that extends distally from a catheter connection portion 1112. A narrowed neck portion 1107 connects the catheter connection portion 1112 to the solid or tubular portion 1105. The solid or tubular portion 1105 extends beyond the at least one guiding member 1104 to a distal solid or tubular tip 1106. The guiding members 1104 are substantially solid or tubular guiding members radiating from the tubular portion 1105 of the tip portion 1102. In the example shown in FIGS. 11A-11C, the substantially solid or tubular guiding members comprise a spherical tip 1110 to provide a less traumatic structure moving through the patient's blood vessels.

Figure 12A:
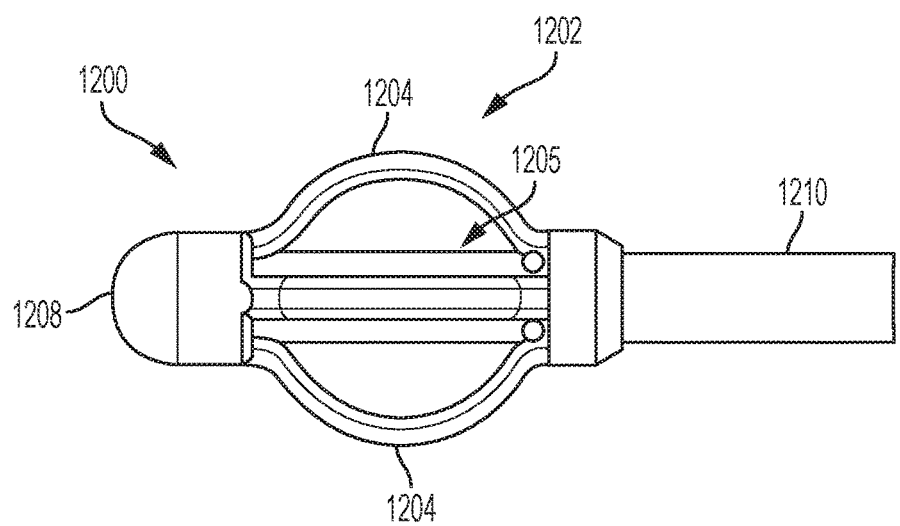
FIGS. 12A-12C are different views of another example catheter guiding tip.
Figure 12B:
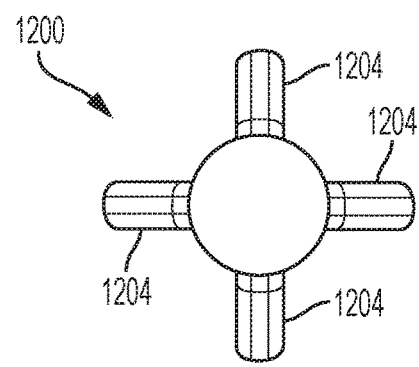
Figure 12C:
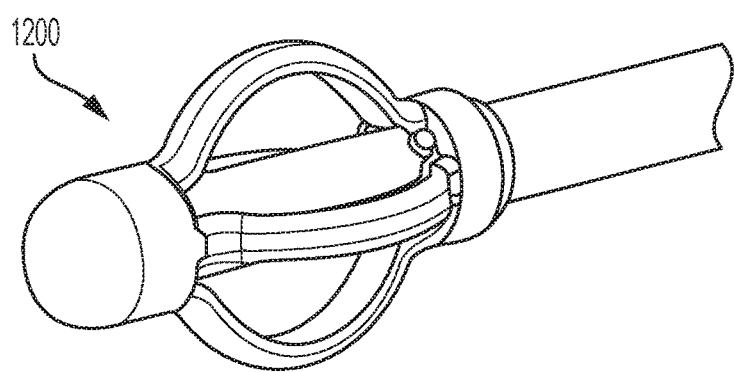

FIGS. 12A-12C are different views of another example catheter guiding tip 1200. The catheter guiding tip 1200 includes a tip portion 1202 comprising a plurality of guiding members 1204 extending radially from a solid or tubular portion 1205 that extends distally from a catheter connection portion 1210. The solid or tubular portion 1205 extends beyond the at least one guiding member 1204 to a distal tubular tip 1208. The guiding members 1204 in FIGS. 12A-12C extend longitudinally and radially outward from the solid or tubular portion 1205 then radially inward to connect back to the solid or tubular portion 1205. The plurality of guiding members 1204 in FIGS. 12A-12C substantially form a bulbous shaped frame having a size that prevents the tip portion 1202 from entering smaller blood vessels during deployment of the catheter.

Figure 13A:
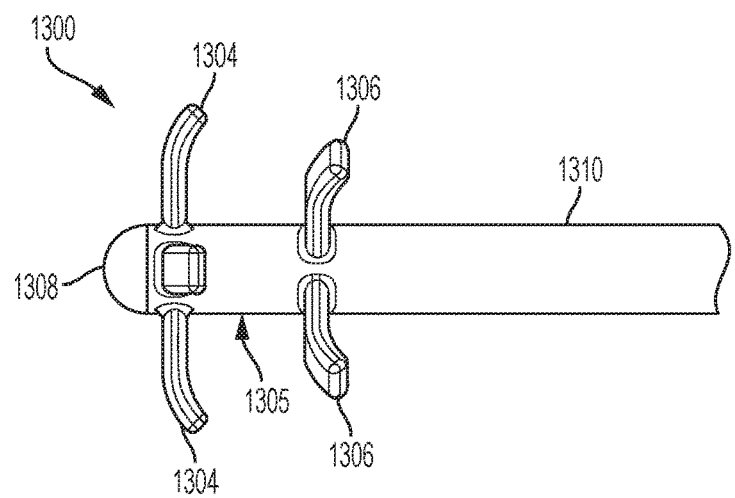
FIGS. 13A-13C are different views of another example catheter guiding tip.
Figure 13B:
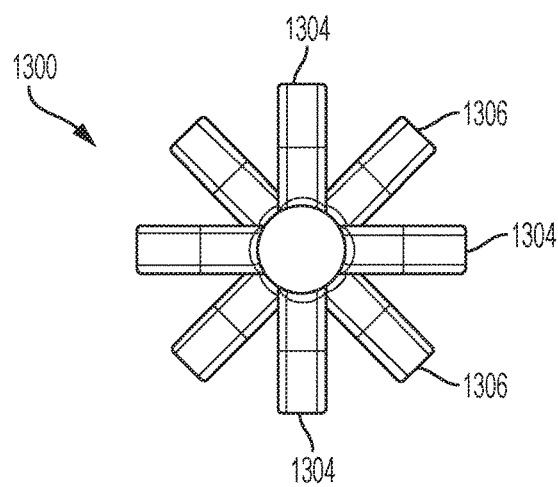
Figure 13C:
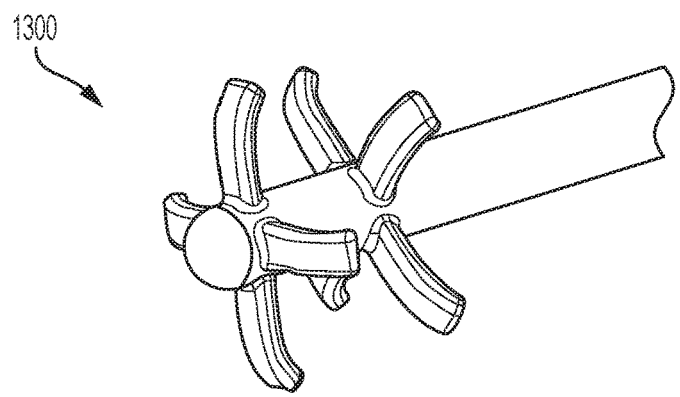

FIGS. 13A-13C are different views of another example catheter guiding tip 1300. The catheter guiding tip 1300 includes a tip portion 1302 comprising a first plurality of guiding members 1306 and a second plurality of guiding members 1304 extending radially from a solid or tubular portion 1305 that extends distally from a catheter connection portion 1310. The second plurality of guiding members 1304 extends radially from the solid or tubular portion 1305 at a point distal to the first plurality of guiding members 1306 and proximal to a distal solid or tubular tip 1308 at a distal end of the solid or tubular portion 1305. The first plurality of guiding members 1306 and the second plurality of guiding members 1304 are flattened perpendicular to the longitudinal axis of the catheter connection portion 110. The first plurality of guiding members 1306 extends from the solid or tubular portion 1305 at an angular shift relative to the second plurality of guiding members 1304. In the example shown in FIGS. 13A-13C, the four first guiding members 1306 extend at 90° from one another. The four second guiding members 1304 extend at 90° from one another and at 45° relative to the four first guiding members 1306.

Figure 14A:
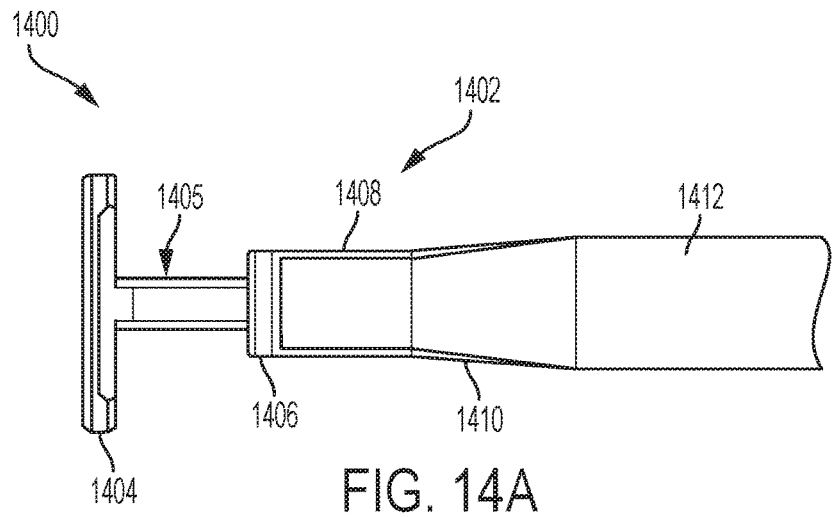
FIGS. 14A-14C are different views of another example catheter guiding tip.
Figure 14B:
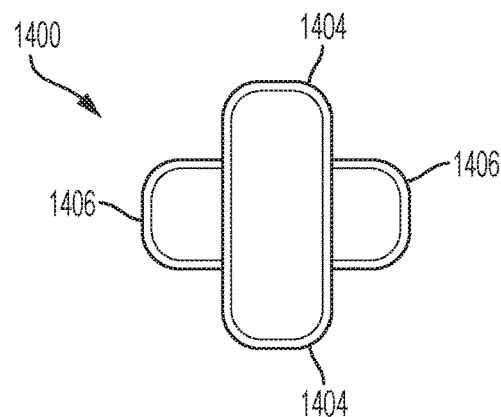
Figure 14C:
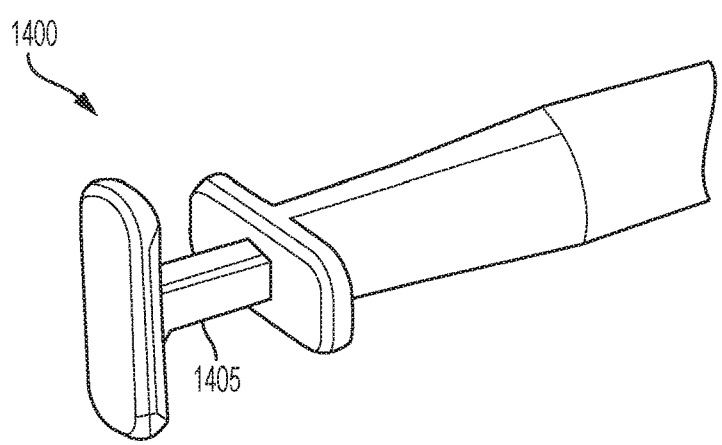

FIGS. 14A-14C are different views of another example catheter guiding tip 1400. The catheter guiding tip 1400 includes a tip portion 1402 comprising a first plurality of guiding members 1406 and a second plurality of guiding members 1404 extending radially from a catheter extension 1405 that extends distally from a catheter connection portion 1412. The second plurality of guiding members 1404 extends radially from the solid or tubular portion 1405 at a distal end of the catheter extension 1405. The first plurality of guiding members 1406 extends from the catheter extension 1405 at a point proximal to the second plurality of guiding members 1404. The first plurality of guiding members 1406 and the second plurality of guiding members 1404 are flattened perpendicular to the longitudinal axis of the catheter member 1412. The first plurality of guiding members 1406 extend from the catheter extension 1405 at an angular shift relative to the second plurality of guiding members 1404. In the example shown in FIGS. 14A-14C, the two first guiding members 1406 extend at 180° from one another. The two second guiding members 1404 extend at 180° from one another and at 90° relative to the two first guiding members 1406.

Figure 15A:
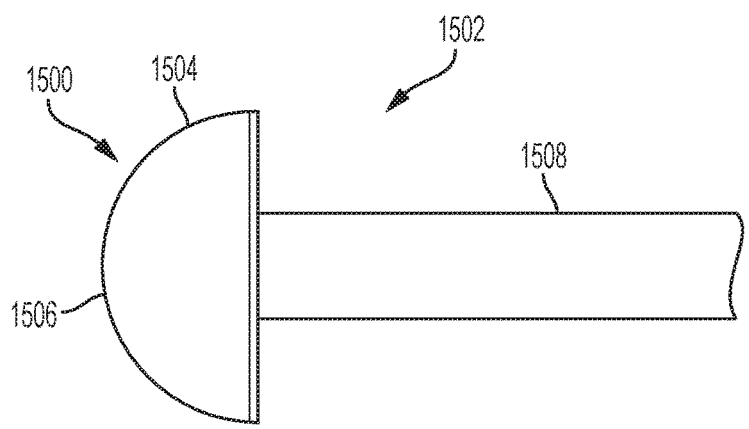
FIGS. 15A-15C are different views of another example catheter guiding tip.
Figure 15B:
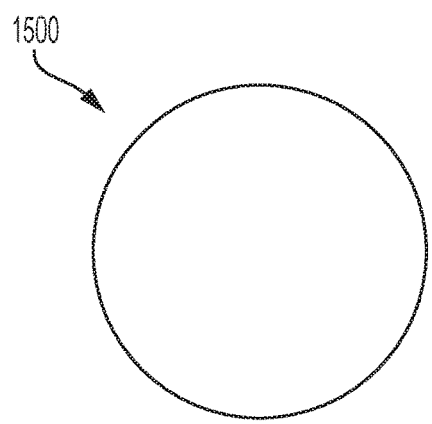
Figure 15C:
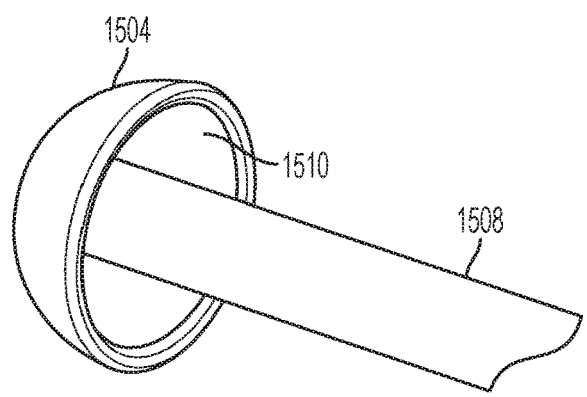

FIGS. 15A-15C are different views of another example catheter guiding tip 1500. The catheter guiding tip 1500 includes a tip portion 1502 at a distal tip 1506 of a catheter connection portion 1508. The tip portion 1502 is a hemisphere shape 1504 extending proximally from the distal tip 1506 at the most distal point of the tip portion 1502. The hemisphere shape 1504 preferably is a hollow hemisphere 1510 so that the tip portion 1502 is more easily compressible.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A device for guiding a catheter through a patient's blood vessels comprising:
a catheter guiding tip extending distally at a distal end of the catheter with an outer dimension substantially the same as an outer dimension of the catheter, the catheter guiding tip expanding distally to at least one guiding member with a tip portion having a shape in an uncompressed state that is larger than the catheter outer dimension along at least one axis perpendicular to a longitudinal axis of the catheter, the catheter guiding tip portion being deformable for insertion in a sheath larger than the tip portion when the tip portion is compressed but smaller than the tip portion when the tip portion is not compressed and resilient for resuming the shape in the uncompressed shape when not subject to compression forces, wherein the shape of the tip portion in the uncompressed state is formed as a member extending distally and radially to form a substantially hook-shaped member along an axis perpendicular to the longitudinal axis of the catheter, and the tip portion transitions to a flattened cross-section as the tip portion hooks around to the most distal point of the tip portion.

2. The device of claim 1, wherein the tip portion hooks circularly around such that a most distal point of the tip portion is positioned near a transition point where the catheter begins to extend radially to form the tip portion.

3. The device of claim 1, wherein the tip portion hooks circularly around such that a most distal point of the tip portion is positioned distal to a transition point where the catheter begins to extend radially to form the tip portion so that the tip portion spirals inward.

4. The device of claim 1, wherein the tip portion is one of a solid member or a tubular member.

5. The device of claim 1, wherein the tip portion is formed by injection molded plastic.

6. The device of claim 1, wherein the tip portion comprises a pre-shaped nitinol member.

7. The device of claim 6, wherein the catheter is a nitinol wire and the tip portion is formed as an extension of a nitinol wire.

8. The device of claim 1, wherein the tip portion is formed as an extension of the catheter.

9. A device for guiding a catheter through a patient's blood vessels comprising:
a catheter guiding tip extending distally at a distal end of the catheter with an outer dimension substantially the same as an outer dimension of the catheter, the catheter guiding tip expanding distally to at least one guiding member with a tip portion having a shape in an uncompressed state that is larger than the catheter outer dimension along at least one axis perpendicular to a longitudinal axis of the catheter, the catheter guiding tip portion being deformable for insertion in a sheath larger than the tip portion when the tip portion is compressed but smaller than the tip portion when the tip portion is not compressed and resilient for resuming the shape in the uncompressed shape when not subject to compression forces, wherein the tip portion comprises a first plurality of guiding members extending radially from a portion that extends beyond the at least one guiding member to a distal extension, and a second plurality of guiding members extending radially from the portion from which the guiding members extend at a point distal to the first plurality of guiding members and proximal to the distal tubular extension.

10. The device of claim 9, wherein the first and second plurality of guiding members are substantially flattened members radiating from the portion from which the respective guiding members extend.

11. The device of claim 10, wherein the first and second plurality of guiding members are flattened longitudinally along the portion from which the respective guiding members extend.

12. The device of claim 10, wherein the first and second plurality of guiding members are flattened perpendicular to the longitudinal axis of the catheter.

13. The device of claim 9, wherein the first and second guiding members are substantially tubular guiding members extending radially from a tubular portion of the tip portion from which the respective guiding members extend.

* * * * *